US008808718B2

(12) United States Patent
Van Der Waal et al.

(10) Patent No.: US 8,808,718 B2
(45) Date of Patent: Aug. 19, 2014

(54) HYPERTONIC ORGANIC ACID OR SALT THEREOF DISINFECTANT COMPOSITION AND ITS USE IN DENTAL TREATMENT

(75) Inventors: Suzette Veronica Van Der Waal, Alphen aan den Rijn (NL); Stanley Brul, Capelle aan de Ijssel (NL); Johannes Jacob De Soet, Naarden (NL); Lucas Wilhelmus Maria Van Der Sluis, St. Robert (FR)

(73) Assignee: Nikinc Pharma B.V., Eindhoven (NL)

( * ) Notice: Subject to any disclaimer, the term of this patent is extended or adjusted under 35 U.S.C. 154(b) by 2 days.

(21) Appl. No.: 13/579,577

(22) PCT Filed: Feb. 18, 2011

(86) PCT No.: PCT/NL2011/050118
§ 371 (c)(1), (2), (4) Date: Sep. 11, 2012

(87) PCT Pub. No.: WO2011/102724
PCT Pub. Date: Aug. 25, 2011

(65) Prior Publication Data
US 2012/0328708 A1 Dec. 27, 2012

Related U.S. Application Data

(60) Provisional application No. 61/305,691, filed on Feb. 18, 2010.

(30) Foreign Application Priority Data

Feb. 18, 2010 (NL) ........................... 2004260

(51) Int. Cl.
*A61K 8/02* (2006.01)
*A61K 47/26* (2006.01)
*A61K 9/00* (2006.01)
*A61K 6/00* (2006.01)
*A61K 47/12* (2006.01)

(52) U.S. Cl.
CPC ............ *A61K 9/006* (2013.01); *A61K 47/26* (2013.01); *A61K 6/0035* (2013.01); *A61K 47/12* (2013.01)
USPC .......................................... 424/405

(58) Field of Classification Search
CPC ...... A61K 9/006; A61K 6/0035; A61K 47/12
See application file for complete search history.

(56) References Cited

U.S. PATENT DOCUMENTS

| 6,368,788 B1 | 4/2002 | Kozhemyakin et al. |
| 2002/0022667 A1 | 2/2002 | Pace et al. |

FOREIGN PATENT DOCUMENTS

| WO | 00/06108 A1 | 2/2000 |
| WO | 01/89520 A2 | 11/2001 |

OTHER PUBLICATIONS

Sathorn, et al., "Antibacterial efficacy of calcium hydroxide intracanal dressing: a systematic review and meta-analysis", International Endodontic Journal, 40, pp. 2-10, 2007.

(Continued)

*Primary Examiner* — Carlos Azpuru
(74) *Attorney, Agent, or Firm* — Gianna Julian-Arnold; Saul Ewing LLP

(57) ABSTRACT

The present invention concerns a disinfectant or antimicrobial composition for use in dental treatment, such as treatment and/or prevention of periodontitis, gingivitis or other forms of oral infection. The present Inventor found that microorganisms that infect the dental tissues and cause inflammation thereof, are susceptible to osmotic stress, to such extent that the application of a hypertonic composition is effective in curing or preventing infection and/or inflammations. It was furthermore found that these microorganisms are also susceptible to acidic stress. The present invention therefore provides compositions that induce osmotic stress in microorganisms causing infection of dental tissue when topically applied thereto, preferably osmotic as well as acidic stress. The present invention also concerns the methods and uses involving the compositions of the invention.

7 Claims, 2 Drawing Sheets

(56) References Cited

OTHER PUBLICATIONS

Sathorn, et al., "Effective of Single- versus multiple-visit endodontic treatment of teeth with apical periodontitis: a systematic review and meta-analysis", International Endodontic Journal, 38, pp. 347-355, 2005.

Sedgley, et al., "Survival of *Enterococcus faecalis* in root canals ex vivo", International Endodontic Journal, 38, pp. 735, 742, 2005.

Seltzer, et al., "Endodontic failures—An analysis based on clinical, roentgenographic, and histologic findings—Part I", Endodontics, Oral Surg Oral Med Oral Pathol, vol. 23, No. 4, pp. 500-516, Apr. 1967.

Seltzer, et al., "Endodontic failures—An analysis based on clinical, roentgenographic, and histologic findings—Part II", Endodontics, Oral Surg Oral Med Oral Pathol, vol. 23, No. 4, pp. 517-530, Apr. 1967.

Siqueira, et al., "Mechanisms of antimicrobial activity of calcium hydroxide: a critical review", International Endodontic Journal, 32, pp. 361-369, 1999.

Siqueira, et al., "Polymerase chain reaction—based analysis of microorganisms associated with failed endodontic treatment", Oral Surg Oral Med Oral Pathol Oral Radiol Endod, 97, pp. 85-94, 2004.

Siren, et al., "Microbiological findings and clinical treatment procedures in endodontic cases selected for microbiological investigation", International Endodontic Journal, 30, pp. 91-95, 1997.

Sjogren, et al., "The antimicrobial effect of calcium hydroxide as a short-term intracanal dressing", International Endodontic Journal, 24, pp. 119-125, 1991.

Sperber, William H., "Influence of Water Activity on Foodborne Bacteria—A Review", Journal of Food Protection, vol. 46, No. 2, pp. 142-150, Feb. 1983.

Stuart, et al., "The comparative antimicrobial effect of calcium hydroxide", Oral Surg Oral Med Oral Pathol, 72, pp. 101-104, 1991.

Stuart, et al., "*Enterococcus faecalis*: Its Role in Root Canal Treatment Failure and Current Concepts in Retreatment", Journal of Endodontics, vol. 32, No. 2, pp. 93-98, 2006.

Sundqvist, et al., "Microbiologic analysis of teeth with failed endodontic treatment and the outcome of conservative re-treatment", Oral Surg Oral Med Oral Pathol Oral Radiol Endod, 85, pp. 96-93, 1998.

Yoon, et al., "*Pseudomonas aeruginosa* Anaerobic Respiration in Biofilms: Relationships to Cystic Fibrosis Pathogenesis", Development Cell, vol. 3, pp. 593-603, Oct. 2002.

Vertucci, Frank J., "Root canal anatomy of the human permanent teeth", Oral Surg. 58, pp. 589-599, 1984.

Waltimo, et al., "Clinical Efficacy of Treatment Procedures in Endodontic Infection Control and One Year Follow-Up of Periapical Healing", Journal of Endodontic, vol. 31, No. 12, pp. 863-866, Dec. 2005.

Watnick, et al., "Minireview", Journal of Bacteriology, vol. 182, No. 10, pp. 2675-2679, May 2000.

Weiger, et al., "Influence of calcium hydroxide intracanal dressings on the prognosis of teeth with endodontically induced periapical lesions", International Endodontic Journal, 33, pp. 219-226, 2000.

Weiger, et al., "Vitality status of microorganisms in infected human root dentine", International Endodontic Journal, 35, pp. 166-171, 2002.

Wijnker, et al., "Antimicrobial properties of salt (NaCl) used for the preservation of natural casings", Food Microbiology, 23, pp. 657-662, 2006.

Wilson, M., "Susceptibility of biofilms of *Streptococcus sanguis* to chlorhexidine gluconate and cetylpyridinium c", Oral Microbiology and Immunology, 11, pp. 188-192, 1996.

Wu, et al., "Prevalence and extent of long oval canals in the apical third", Oral Surg Oral Med, Oral Pathol Oral Rediol Endod, vol. 89, No. 6, pp. 739-743, Jun. 2000.

Portenier, et al., "The Susceptibility of Starved, Stationary Phase, and Growing Cells of *Enterococcus faecalis* to Endodontic Medicaments", Journal of Endodontics, vol. 31, No. 5, pp. 380-386, May 2005.

Abdullah, et al., "Susceptibilties of Two *Enterococcus faecalis* Phenotypes to Root Canal Medications", Journal of Endodontics, vol. 31, No. 1, pp. 30-36, Jan. 2005.

Adriao, et al., "Marked intra-strain variation in response to *Listeria monocytogenes* dairy isolates to acid or salt stress and the effect of acid or salt adaptation on adherence to abiotic surfaces", International Journal of Food Microbiology, 123, pp. 142-150, 2008.

Ang, et al., "Chemical and physical aspects of cleaning of organic-fouled reverse osmosis membranes", Journal of Membrane Science, 272, pp. 198-210, 2006.

Bautista, Gallego J., "Individual Effects of Sodium, Potassium, Calcium, and Magnesium Chloride Salts on *Lactobacillus pentosus* and *Saccharomyces cerevisiae* Growth", Journal of Food Protection, vol. 71, No. 7, pp. 1412-1421, 2008.

Bystrom, A., "The Antibacterial effect of camphorated paramonochlorophenol, camphorated phenol and calcium hydroxi", Endod Dent Traumatol, 1, pp. 170-175, 1985.

De Paz, Luis Chavez, "Redefining the Persistent Infection in Root Canals: Possible Role of Biofilm Communities", Journal of Endodontics, vol. 33, No. 6, pp. 652-662, Jun. 2007.

De Paz, et al., "Response to alkaline stress by root canal bacteria in biofilms", International Endodontic Journal, 40, pp. 344-355, 2007.

Costerton et al., "Microbial Biofilms", Annu. Rev. Microbiol, 49, pp. 711-745, 1995.

Csonka, Laszlo N., "Physiological and Genetic Responses of Bacteria to Osmotic Stress", Microbiological Reviews, vol. 53, No. 1, pp. 121-147, Mar. 1989.

Csonka, et al., "Prokaryotic Osmoregulation: Genetics and Physiology", Annu. Rev. Microbiol. 45, pp. 569-606, 1991.

Deng, et al., "Influence of *Streptococcus mutans* on *Enterococcus faecalis* Biofilm Formation", Journal of Endodontics, vol. 35, No. 9, pp. 1249-1252, Sep. 2009.

Estrela, et al., "Accuracy of Cone Beam Computed Tomography and Panoramic and Periapical Radiography for Detection of Apical Periodontitis", Journal of Endodontics, vol. 34, No. 3, pp. 273-279, Mar. 2008.

Evans, et al., "Mechanisms involved in the resistance of *Enterococcus faecalis* to calcium hydroxide", International Endodontic Journal, 35, pp. 221-228, 2002.

Facklam, R. R., "Comparison of Several Laboratory Media for Presumptive Identification of Enterococci and Group D Streptococci", Applied Microbiology, vol. 26, No. 2, pp. 138-145, Aug. 1973.

Fan, et al., "C-shaped Canal System in Mandibular Second Molars: Part I—Anatomical Features", Journal of Endodontics, vol. 30, No. 12, pp. 899-903, Dec. 2004.

Ferreira, et al., "Antimicrobial effect of propolis and other substances against selected endodontic pathogens", Oral Surg Oral Med Oral Pathol Oral Radiol Endod, vol. 104, pp. 709-716, 2007.

Figdor, et al., "Starvation survival, growth and recovery of *Enterococcus faecalis* in human serum", Oral Microbiology and Immunology, vol. 18, pp. 234-239, 2003.

Georgopoulou, et al., "Evaluation of the antimicrobial effectiveness of citric acid and sodium hypochlorite on the anaerobic flora of the infected root canal", International Endodontic Journal, vol. 27, pp. 139-143, 1994.

Gutierrez, et al, "Physiology of the osmotic stress response in microorganisms", International Journal of Food Microbiology, 28, pp. 233-244, 1995.

Haapasalo, et al., "In vitro infection and of Dentinal Tubules", Journal of Dental Research, vol. 66, No. 8, pp. 1375-1379, Aug. 1987.

Kakahashi, et al., "The effects of surgical exposures of dental pulps in germ-free and conventional laboratory rats", Oral Surg Oral Med Oral Pathol, vol. 20, No. 3, pp. 340-349, Sep. 1965.

Kara, et al., "Microstructural differences between single-species and dual-species biofilms of *Streptococcus mutans* and *Veillonella parvula*, before and after exposure to chlorhexidine", FEMS Microbiol Lett 271, pp. 90-97, 2007.

Kishen, et al., "*Enterococcus faecalis*-mediated biomineralized biofilm formation on root canal dentine in vitro", Journal of Biomedical Material Research Part A, vol. 77A, Issue 2, pp. 406-415, 2006, at http://www.interscience.wiley.com.

(56) References Cited

OTHER PUBLICATIONS

Lattner, et al., "C-NMR study of the interaction of bacterial alginate with bivalent cations", International Journal of Biological Macromolecules, 33, pp. 81-88, 2003.

Lee, Wie-Shing, "Improved Procedure for Identification of Group D Enterococci with Two New Media", Applied Microbiology, vol. 24, No. 1, pp. 1-3, Jul. 1972.

Lee, et al., "Salt cleaning of organic-fouled reverse osmosis membranes", ScienceDirect, Water Research 41, pp. 1134-1142, 2007.

Lin, L. M., "Factors associated with endodontic treatment", Journal of Endodontics, vol. 18, No. 12, pp. 625-627, Dec. 1992.

Molander, et al., "Microbiological status of root-filled teeth with apical periodontitis", International Endodontic Journal, 31, pp. 1-7, 1998.

Molander, et al., "Clinical and Radiographic Evaluation of One- and Two-visit Endodontic Treatment of Asymptomatic Necrotic Teeth with Apical Periodontitis: A Randomized Clinical Trail", CONSORT Clinical Trial, vol. 33, No. 10, pp. 1145-1148, Oct. 2007.

Morfis, et al., "Study of the apices of human permanent teeth with the use of a scanning electron microscope", Endodontics, vol. 77, No. 2, pp. 172-176, Feb. 1994.

Nair, et al., "Microbial status of apical root canal system of human mandibular first molars with primary apical periodontitis after "one-visit" endodontic treatment", Oral Surg Oral Med Oral Pathol Oral Radiol Endod, vol. 99, No. 2, pp. 231-252, Feb. 2005.

Nakajo, et al., "Resistance to acidic and alkaline environments in the endodontic pathogen *Enterococcus faecalis*", Oral Microbology and Immunology, vol. 21, pp. 283-288, 2006.

Ozok, et al., "Comparison of Growth and Susceptibility to Sodium Hypochlorite of Mono- and Dual-Species Biofilms of *Fusobacterium nucleatum* and Peptostreptosoccus (*Micromonas*) micros", Journal of Endodontics, vol. 33, No. 7, pp. 819-822, Jul. 2007.

Peters, et al., "Effects of instrumentation, irrigation and dressing with calcium hydroxide on infection in pulpless teeth with periapical bone lesions", International Endodontic Journal, vol. 35, pp. 13-21, 2002.

Pichereau, et al., "The osmoprotectant glycine betaine inhibits salt-induced cross-tolerance towards lethal treatment in *Enterococcus faecalis*", Microbiology, 145, pp. 427-435, 1999.

Vanhaecke, et al., "Kinetics of *Pseudomonas aeruginosa* Adhesion to 304 and 316-L Stainless Steel: Role of Cell Surface Hydrophobicity", Applied and Environmental Microbiology, vol. 56, No. 3, pp. 788-795, Mar. 1990.

Ranta, et al., "Monoinfection of root canal with *Pseudomonas aeruginosa*", Endod Dent Traumatol, 4, pp. 269-272, 1988.

Record, et al., "Reponses of *E. coli* to osmotic stress: large changes in amounts of cytoplasmic solutes and water", TIBS 23, pp. 143-148, Apr. 1998.

Sarkisova, et al., "Calcium-induced Virulence Factors Associated with the Extracellular Matrix of Mucoid *Pseudomonas aeruginosa* Biofilms", Journal of Bacteriology, vol. 187, No. 13, pp. 4327-4337, Jul. 2005.

Sathorn, et al., "How Useful is Root Canal Culturing in Predicting Teratment Outcome?", Journal of Endodontics, vol. 33, No. 3, pp. 220-225, Mar. 2007.

International Search Report, dated Jun. 9, 2011, issued in priority International Application No. PCT/NL2011/050118.

HYPERTONIC ORGANIC ACID OR SALT THEREOF DISINFECTANT COMPOSITION AND ITS USE IN DENTAL TREATMENT

CROSS REFERENCE TO RELATED APPLICATIONS

This application claims the priority of PCT/NL2011/050118, filed on Feb. 18, 2011, which claims priority to U.S. provisional Application No. 61/305,691, filed Feb. 18, 2010 and Netherlands Application No. 2004260, filed Feb. 18, 2010, the entire contents of all of which are hereby incorporated in total by reference.

FIELD OF THE INVENTION

The present invention concerns a disinfectant or antimicrobial composition that is suitable for use in dental treatment. More in particular, the present invention concerns compositions for use in treating or preventing apical, lateral or marginal periodontitis, gingivitis, peri-implantitis or other forms of oral infection, especially during endodontic and/or periodontic treatments or implant surgery, especially during root canal treatment. The present invention also concerns such methods and uses involving the compositions of the invention.

BACKGROUND OF THE INVENTION

Microorganisms in the root canal system and their by-products cause pulpal and periapical inflammation (Kakehashi et al. 1965). Therefore incomplete disinfection of the root canal system is considered to be a major cause of persisting apical periodontitis (Seltzer & Bender 1967, Lin et al. 1992). Elimination of the microbial infection is one of the main goals of root canal treatment. Despite serious efforts, however, histologic and cultivation studies confirm the presence of persisting microorganisms after root canal treatment (Nair et al. 2005). One of the reasons of our inability to completely disinfect the root canal system is the complexity of its architecture (Vertucci 1984, Wu et al. 2000).

Another reason is that microorganisms like bacteria live in a bio film configuration (Costerton et al. 1995, Watnick & Kolter 2000). This makes them more resistant to endodontic treatment procedures. Thorough mechanical cleaning of the root canal system is impossible due to its complex morphology. Mechanical filing is performed to enable irrigation with antimicrobials. Current root canal irrigants have a superficial working range. The most potent disinfectant sodium hypochlorite does not penetrate lateral from the main canal due to its reactive nature. Inactivation occurs as soon as sodium hypochlorite encounters organic matter (Moorer & Wesselink 1982). Chlorhexidine does not penetrate into a biofilm (Zaura-Arite et al. 2001).

Irrigants like IKI (IPI), ethylalcohol or chlorhexidine are less effective in debriding the root canal system because they lack tissue dissolving properties.

On average 4 million CFU per tooth persist after chemo-mechanical debridement. Residual bacteria and other microorganisms that have access to the periapical tissues via accessory canals, sustain a chronic inflammatory process. Depending on the type of tooth, apical branching occurs in up to fifty percent of the teeth. Chronic infection and inflammation are responsible for failure of the endodontic therapy. Failure rates will increase with the introduction of CBCT (Cone Beam Computerized Tomography) due to the increase in detection of failure (Estrela et al. 2008). Root canal treatments are performed in two ways: i) one session in the dentist's chair, with NaOCl as disinfecting irrigant or ii) two or more sessions involving irrigation with NaOCl, while in between the sessions calcium hydroxide ($Ca(OH)_2$) is enclosed in the root canal for further disinfection.

$Ca(OH)_2$ is currently used as intracanal dressing in between two treatment sessions. With its pH of 12, $Ca(OH)_2$ is weakly bactericidal. This is reported in several studies on bacterial suspensions (planktonic bacteria). In subjects diagnosed with apical periodontitis $Ca(OH)_2$ is administered to reach additional disinfection and to prevent regrowth of the intracanal flora in between two treatment sessions.

Antimicrobial agents used in endodontics have certain disadvantages. For instance calcium hydroxide is only effective when it is in direct contact with the microorganisms (Siqueira & Lopes 1999). Furthermore, $Ca(OH)_2$ is only bactericidal to some species, provoking a shift in the microbial flora towards more resistant species (Nakajo et al. 2006). $Ca(OH)_2$ cannot eradicate *E. faecalis*, associated with failing endodontic treatments (Sirén et al. 1997, Sundqvist et al. 1998). Long term application of $Ca(OH)_2$ weakens the dentine and remnants of the $Ca(OH)_2$-paste are difficult to remove.

In our study interesting findings were observed. Dual-species bio films were exposed to $Ca(OH)_2$. After an initial hundredfold bacterial reduction, the bacterial counts recuperated to a tenfold reduction after a week (end of experiment). This sheds doubts on the antibacterial efficacy of $Ca(OH)_2$ on a biofilm. Furthermore the calcium hydroxide groups showed calcification of the biofilm in which the viable colonies harbored (Observation with confocal laser scanning microscopy after Dead/Live stain). The calcified plaque could not be removed from the model by swabbing with a cotton pellet or scraping with a hard plastic device. This was an interesting finding of the study because $Ca(OH)_2$ is the only well accepted intracanal medicament in the world. If this calcification also occurs in the root canal, then this will hamper disinfection even more.

It is an objective of the present invention to provide improved disinfectant or antimicrobial compositions that can aid in overcoming the disadvantages of the treatments currently available.

SUMMARY OF THE INVENTION

The present Inventor has surprisingly found that microorganisms that typically infect the dental tissues and cause inflammation thereof are susceptible to osmotic stress, to such extent that the application of a hypertonic composition to the infected tissue or the tissue that is at risk of becoming infected, will cure or prevent infection and/or inflammations resulting therefrom. Without wishing to be bound by any particular theory, it is hypothesized that due to osmotic stress the microorganisms like bacteria, which cause inflammation, become metabolically exhausted, leading to their death.

It was furthermore found that the microorganisms involved in dental tissue infections are also susceptible to acidic stress. Without wishing to be bound by any particular theory, it is hypothesized that acidic stress also aids to metabolic exhaustion of the microorganisms like bacteria that cause inflammation. It is further hypothesized that the combination of osmotic and acidic stress will more rapidly lead to death of the microorganisms than application of either one of these stress factors individually.

The present invention therefore provides compositions that induce osmotic stress in microorganisms causing infection of dental tissue when topically applied thereto. In a particularly preferred embodiment of the invention compositions are provided that induce osmotic as well as acidic stress in microorganisms causing infection of dental tissue when topically applied thereto.

In addition, the present invention provides the use of the above compositions in dental treatment, especially for treating or preventing apical, lateral or marginal periodontitis, gingivitis, peri-implantitis or other forms of oral infection, e.g. during endodontic and/or periodontic treatments, such as root canal treatment.

Furthermore, the present invention provides methods of dental treatment, especially methods of treating or preventing apical, lateral or marginal periodontitis, gingivitis, peri-implantitis or other forms of oral infection, e.g. during endodontic and/or periodontic treatments or during implant surgery, such as root canal treatment, involving the use of the compositions causing osmotic and, optionally, acidic stress.

Furthermore, the present invention provides the use of tonicity agents in the manufacture of a medicament for use in dental treatment, especially in treating or preventing apical, lateral or marginal periodontitis, gingivitis, peri-implantitis or other forms of oral infection, e.g. during endodontic and/or periodontic treatments or during implant surgery, especially during root canal treatment.

DETAILED DESCRIPTION OF THE INVENTION

Figure 1:
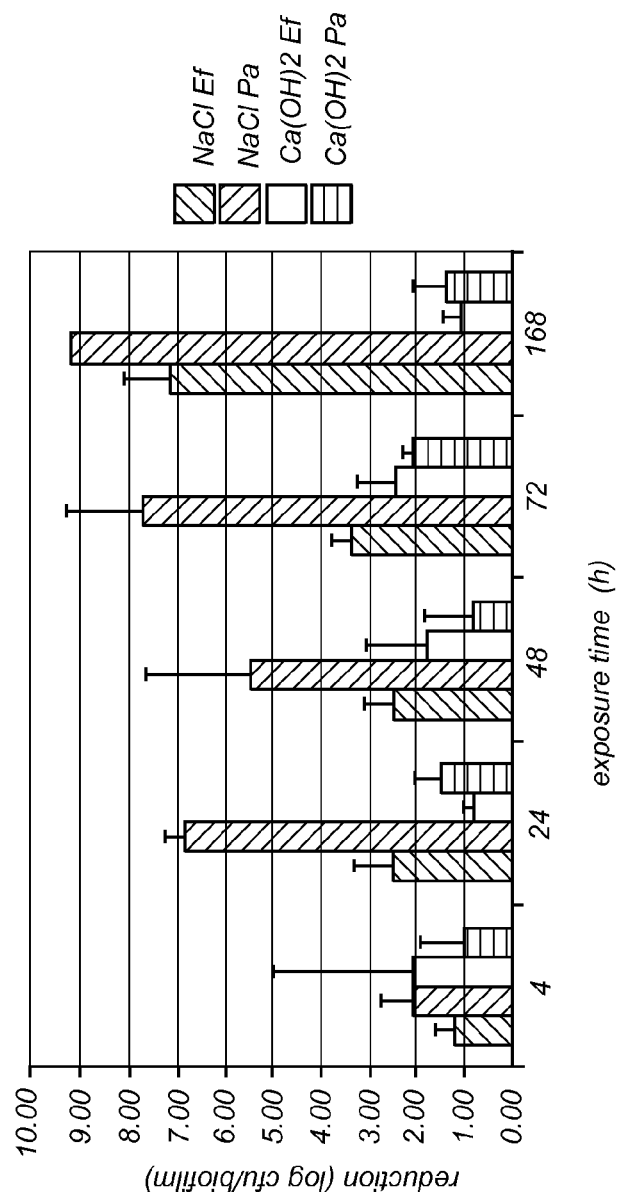
FIG. 1: Effect of NaCl and $Ca(OH)_2$ on reduction of $E.$ $Faecalis$ and $P.$ $aeruginosa$. The graph shows the reduction in CFU counts of bacterial species in log CFU/biofilm after exposure (hours) to NaCl and $Ca(OH)_2$. The negative controls contained on average $2.0 \times 10^8$ CFU $E.$ $faecalis$ and $3.5 \times 10^8$ CFU $P.$ $aeruginosa$, which numbers increased in time.

Hence, in a first aspect a composition is provided comprising a tonicity agent in an amount which renders the composition hypertonic, which composition is suitable for use as a disinfectant or antimicrobial preparation in dental treatment.

In this document and in its claims, the verb 'to comprise' and its conjugations are used in their non-limiting sense to mean that items following the word are included, without excluding items not specifically mentioned. In addition, reference to an element by the indefinite article 'a' or 'an' does not exclude the possibility that more than one of the element is present, unless the context clearly requires that there be one and only one of the elements. The indefinite article 'a' or 'an' thus usually means 'at least one'.

The 'composition' of the invention typically comprises a combination of two or more distinct substances and typically will be in solid, semi-solid, or liquid form, wherein semi-solid refers to a rheology typical of pseudoplastic or plastic fluids. Suitable examples include powders, dispersions, emulsions, suspensions and solutions. As indicated above, the composition of the invention is suitable for use in dental treatment, which means that the composition is suitable for application in the oral cavity of a human. Therefore, the composition is typically 'physiologically acceptable', i.e. it does not contain any ingredients in amounts that, when applied in the oral cavity of a human subject, would cause harm to said subject to an extent outweighing any beneficial effects.

As used herein, the term 'tonicity agent' encompasses any substance that can be dissolved in water such as to produce a difference in tonicity or water potential. In general, the tonicity agent may be an inorganic or organic salt, a low molecular weight molecule or a (water-soluble) polymer. In principle, tonicity is a colligative property, i.e. it depends on the concentration of the solute but not on its identity. Hence, in the context of the present invention, the suitability of a given agent for use as the tonicity agent will depend on its solubility, highly water-soluble agents typically being preferred over sparingly water-soluble agents, and on its ability to (passively or actively) cross cell membranes, since solutes can only affect tonicity if a concentration difference can be established. Secondary considerations for selecting the most appropriate tonicity agent may typically include physiological tolerability, further biological and/or chemical (re)activity, ease of handling and (other) economical and environmental factors.

In a particularly preferred embodiment of the present invention a composition as defined in any of the foregoing is provided, wherein the osmotic agent is selected from the group consisting of inorganic sodium salts, organic sodium salts, inorganic potassium salts, organic potassium salts, inorganic magnesium salts, organic magnesium salts, sugar alcohols and mixtures thereof, preferably from the group consisting of inorganic sodium salts, organic sodium salts, inorganic magnesium salts, organic magnesium salts, sugar alcohols and mixtures thereof. As is generally known by those skilled in the art, sugar alcohols, also often referred to as polyols, have the general formula $H(HCHO)_{n+1}H$ (sugars having the formula $H(HCHO)_nHCO$) and can also serve as a tonicity agent in accordance with this invention. Some of the sugar alcohols may however also serve as a metabolic substrate or energy source for microorganisms in the dental tissues, and these sugar alcohols are less preferred for the purposes of the present invention. A preferred sugar alcohol is mannitol. In a particularly preferred embodiment of the present invention a composition as defined in any of the foregoing is provided, wherein the osmotic agent is selected from the group consisting of sodium chloride, sodium iodide, magnesium chloride, sodium acetate, sodium sorbate, sodium lactate, sodium formate, potassium acetate, potassium sorbate, potassium lactate and potassium formate, mannitol and mixtures thereof, more preferably from the group consisting of sodium chloride, sodium iodide, magnesium chloride, sodium acetate, sodium sorbate, sodium lactate, sodium formate mannitol and mixtures thereof.

As indicated above, the present composition is a hypertonic composition. 'Hypertonic', in general indicates that a given composition contains a greater concentration of impermeable solutes than another solution, such that a water potential is created when said solutions are placed on opposite sides of a semi-permeable membrane. In the fields of biology and medicine, tonicity is typically employed when describing the response of cells immersed in an external solution. Thus, in the context of the present invention, the term 'hypertonic' indicates that the concentration of solute in the composition is higher than that of cells contacted with the composition, such that water will diffuse out of said cells. For the purpose of the present invention the term 'hypertonic' is typically employed to refer to a composition comprising a solute amount which is sufficient to create a water potential greater than that of human blood, a living cell or, most preferably, the cytosol of a microorganism, such as those typically infecting the dental tissues, causing inflammation thereof.

As will be understood by those skilled in the art, the creation of an osmotic stress inducing environment at the site of treatment of the body, may not only be achieved by applying thereto an aqueous solution of the tonicity agent(s), but also by applying said agent(s) in other forms or formulations, e.g. which contain the tonicity agent in non-dissolved form from which it can dissolve in the physiological fluids present at the site of application. The present invention is not particularly limited in this respect. However, a preferred embodiment of the invention provides a composition as defined in any of the foregoing wherein the composition comprises a hypertonic aqueous solution of the tonicity agent. In the context of this invention the term 'solution' is used to indicate that the composition contains an aqueous phase wherein the tonicity agent has been dissolved; it is not intended to restrict the scope of the invention to compositions consisting exclusively of an aqueous solution phase.

More in particular, in a preferred embodiment of the invention, a composition as defined in any of the foregoing is provided, comprising an aqueous phase containing the tonicity agent in an amount which renders said aqueous phase hypertonic, and one or more other ingredients, examples of which will be given below, each of which may be dissolved in said aqueous phase or may be contained in a distinct phase. Preferably, though not necessarily, the present composition comprises the aqueous phase containing the dissolved tonicity agent as the continuous phase. Thus, in an embodiment of the invention, the composition may take the form of an emulsion, suspension, dispersion or solution comprising a continuous aqueous phase having dissolved therein the tonicity agent in an amount which renders it hypertonic.

As indicated above, a hypertonic environment forces water to leave cells contained in said environment. In eukaryotic cells this will cause the shape of the cell to become distorted and wrinkled, a state known as crenation. In cell wall containing cells, the effect is even more dramatic. The flexible cell membrane pulls away from the rigid cell wall, but remains joined to the cell wall at points called plasmodesmata. The cell takes on the appearance of a pincushion, and the plasmodesmata almost cease to function because they become constricted, a condition known as plasmolysis. Under conditions of high concentrations of solute in the environment, besides water being drawn out of the cells through osmosis, also the transport of substrates and cofactors into the cell is prohibited, thereby inducing (hyperosmotic) 'stress' or 'shock' in the cell. As will be understood by those skilled in the art, the present composition is applied to a site of treatment with the intention to create a hypertonic environment such as to cause (hyper)osmotic stress or shock in the bacteria and/or other micro-organisms present at said site. Bacteria and/or other micro-organisms can possess mechanisms that may enable them to respond to osmotic shock to some extent.

In view of the foregoing considerations it is particularly preferred that the compositions have an osmolarity higher than blood, cells or the cytosol of microorganisms, which is approximately 0.3 osmol/L. Hence, the aqueous phase of the present composition comprises tonicity agent in an amount sufficient for an osmolarity of the composition of at least above 0.5, 1, 2, 5 or 10 osmol/L. As will be understood by those skilled in the art this means that if the tonicity agent is an agent that dissociates into two ions, as is the case for most of the preferred tonicity agents of this invention, this corresponds to a preferred molarity of the composition of e.g. at least 0.25, at least 0.5, at least 1, at least 2.5, at least 3.5 or at least 5.

Furthermore, it is particularly preferred that the aqueous phase of the present composition comprises a tonicity agent in an amount sufficient to create an osmotic value of at least $0.125*10^7$ Pa, at least $0.25*10^7$ Pa, at least $0.5*10^7$ Pa, at least $1.25*10^7$ Pa, at least $2.5*10^7$ Pa, or at least $3*10^7$ Pa. Osmotic value, which is synonymous to osmotic pressure, can simply be calculated by the van't Hoff law, described by the equation $\pi=RTC$, wherein $\pi$ is the osmotic pressure (atm.), R is the ideal gas constant, T is the thermodynamic (absolute) temperature (Kelvin) and C is the total solute concentration expressed as Osmoles of solute per liter of solution, as is generally known in the art.

As noted herein before, the present inventor has found that a mechanism referred to herein as 'organic acid stress' can suitably inhibit the growth of bacteria on dental tissue. Thus, in a preferred embodiment of the present invention, a composition is provided as defined in any of the foregoing, comprising an effective amount of an organic acid and/or an organic acid anion, especially an organic acid and/or an organic acid salt. As will be understood by those skilled in the art a water-soluble organic salt will increase the tonicity of the composition. Hence, in an embodiment of the invention the tonicity agent is selected from the group of organic acid salts, preferably organic acid sodium salts, such as those selected from the group consisting of sodium acetate, sodium sorbate, sodium lactate, sodium formate and mixtures thereof and/or those selected from the group consisting of potassium acetate, potassium sorbate, potassium lactate and potassium formate, and the composition comprises said organic acid salt in an amount which renders the preparation hypertonic. In another embodiment of the invention a composition in accordance with any of the foregoing is provided comprising a combination of tonicity agents, wherein a first agent is present selected from the group of inorganic salts and sugar alcohols, preferably inorganic sodium salts, such as sodium chloride and sodium iodide, inorganic potassium salts, such as potassium chloride and potassium iodide, inorganic magnesium salts, such as magnesium chloride, and mixtures thereof, and a further agent is present selected from the group of organic acids and/or salts thereof, preferably organic acid sodium salts such as sodium acetate, sodium sorbate, sodium lactate, sodium formate, potassium acetate, potassium sorbate, potassium lactate and potassium formate and mixtures thereof, wherein the total amount of said agents renders the composition hypertonic. In another embodiment, a combination of tonicity agents is present, a first agent being selected from the group of inorganic salts and sugar alcohols, preferably inorganic sodium salts, such as sodium chloride and sodium iodide, inorganic magnesium salts, such as magnesium chloride, and mixtures thereof, and a further agent being selected from the group of organic acids and/or salts thereof, preferably organic acid sodium salts such as sodium acetate, sodium sorbate, sodium lactate, sodium formate and mixtures thereof, wherein the total amount of said agents renders the composition hypertonic.

Without wishing to be bound by any particular theory, it is believed that the organic acids are most effective at lower pH. In solution, a weak organic acid exists in equilibrium between the dissociated state and undissociated state. The distribution of the two forms of the acid is determined by its pKa value and the pH of the environment. Consequently, in more acidic environments the equilibrium is shifted to the undissociated form. Charged molecules, like protons and the anion, are unable to pass the lipid membrane. However, the neutral undissociated acid is relatively membrane permeable and able to diffuse over the membrane. Inside the cell a new equilibrium is formed between dissociated and undissociated state. Since most microorganisms exhibit an intracellular pH near neutrality the equilibrium is shifted to the dissociated state of the acid. Consequently, protons are released into the cytosol, lowering the proton gradient. Part of the energy used to build up the proton gradient (for e.g. ATP synthesis) is thereby instantly lost. Depending on the buffering capacity of the cell, the entry of protons can acidify the cytosol. Changes in intracellular pH will affect virtually all biochemical processes, including the redox state, DNA transcription, protein synthesis and folding, enzyme activities, and transport over the membrane.

Since the entry of undissociated acid into the cell is driven by diffusion, this process continues until the concentrations of undissociated acid on the inner and outer membrane leaflets are equal. The higher the initial ph difference between the environment (lower pH) and the inside of the cell (higher pH), the higher the intracellular anion concentration can get.

Furthermore, when comparing organic acids, the growth-inhibitory effect seems to correlate with their membrane solubility, as reflected by the octanol-water partition coefficient (log Kow). To obtain similar reductions in microbial growth rate, usually lower concentrations of more hydrophobic weak organic acids are needed than of more hydrophilic ones. This observed correlation will likely be the consequence of the faster/easier entry of the more hydrophobic weak organic acid into the cell. In conclusion, no single mechanism appears to explain the antimicrobial activity of the organic acids. Their mode of action is believed to relate primarily to dissipation of the proton gradient (uncoupling) and acidification of the cytosol, but other factors such as membrane disruption, and metabolic perturbation by inactivating specific enzymes may be relevant as well.

In keeping with the suggested mechanism of uncoupling and cytosol acidification, the present inventors found that particularly good results can be obtained if the composition is buffered to an acidic pH value. Hence in a preferred embodiment of the invention, a composition is provided as defined herein before, which comprises a buffering system. As will be understood by those skilled in the art, a buffering system typically comprises a combination of a weak acid and its conjugate base. Suitable and generally known examples of physiologically acceptable buffering systems include combinations of citrate/HCl; citric acid/citrate; malic acid/maleate, succinic acid/succinate, acetic acid/acetate, sorbic acid/sorbate, lactic acid/lactate and $M_2HPO_4/MH_2PO_4$ (wherein M is a monovalent cation) Preferably the buffering system is selected from the group consisting of citrate/HCl; citric acid/citrate; malic acid/maleate, succinic acid/succinate, acetic acid/acetate and $M_2HPO_4/MH_2PO_4$. Hence, in an embodiment of the invention a composition is provided as defined herein before, which comprises an osmotic and acidic stress inducing amount of a combination of i) one or more organic acids and/or salts thereof, preferably sodium or potassium salts thereof, most preferably sodium salts thereof, the organic acid preferably being selected from the group of acetic acid, formic acid, sorbic acid and lactic acid; ii) one or more buffering agents, preferably selected from the group consisting of citrate buffer, succinate buffer, maleate buffer, sorbate buffer, acetate buffer, lactate buffer and phosphate buffer, more preferably from the group consisting of citrate buffer, succinate buffer, maleate buffer, acetate buffer, lactate buffer and phosphate buffer and, optionally, iii) one or more additional tonicity agents, preferably selected from inorganic sodium salts, inorganic potassium salts, inorganic magnesium salts and sugar alcohols, more preferably selected from inorganic sodium salts, inorganic magnesium salts and sugar alcohols, most preferably from sodium chloride, magnesium chloride, sodium iodide and mannitol, wherein the total amount of said agents renders the composition hypertonic. In a preferred embodiment, the composition comprises an aqueous solution of the recited components i)-iii). As will be appreciated by those skilled in the art, combining the recited components in an aqueous phase typically yields a system in dynamic equilibrium containing dissolved non and/or partially dissociated organic acid molecules, organic acid anions, inorganic cations and, optionally, inorganic anions.

In a preferred embodiment of the invention a composition as defined in any of the foregoing is provided, wherein the composition is buffered to a pH of below 7. Values of well below 5.5 will still be effective in causing acidic stress, but may also cause decalcification of the tooth enamel and are therefore not preferred. Typically, the composition is buffered to a pH within the range of 5.5-6.7, more preferably within the range of 5.7-6.5, most preferably within the range of 6-6.25. As will be understood by those skilled in the art the optimum pH of the composition will depend inter alia on the choice of the organic acid used as the acidic stress inducing agent.

The present composition may include one or more additional 'active ingredients'. In a preferred embodiment the composition contains one or more additional agents which act as an antimicrobial, antiseptic, microbiocide, bacteriocide, germicide, antibiotic, bacteriocin and/or biofilm inhibitor. Preferred examples of such additional active ingredients include antimicrobial agents, preferably those selected from the group consisting of sodium hypochlorite, EDTA, IPI (iodine potassium iodide, $I_2KI$ or 'Lugol's iodine'), ethylalcohol, chlorhexidine (gluconate), Framycetin (sulfate), beta-lactams, aminoglycosides, triclosan, metronidazole, tetracyclines, quinolones, plant essential oils, camphor, thymol, carvacrol, menthol, eucalyptol, and methyl salicylate, most preferably those selected from the group consisting of sodium hypochlorite, IPI (iodine potassium iodide, $I_2KI$ or 'Lugol's iodine'), ethylalcohol and chlorhexidine. As indicated in the Background part of this document, the use of most of these agents in dental treatment is known in the art. As will be understood by those skilled in the art, despite the fact that treatment with any of these agents alone typically yields inferior results as compared to treatment with the present composition, their incorporation in the present compositions may further enhance, possibly synergistically, the antimicrobial action thereof. It is within the normal capacities of those skilled in the art to determine the appropriate amounts, of such additional ingredients to be incorporated in the present compositions.

Furthermore, the present composition will typically include one or more additional ingredients such as colorants, flavouring agents, medicinal compounds, surface active agents, detergents, stabilizers, viscosity modifiers, diluting agents, flow control additives, polymeric thickeners, preservatives, imaging agents, radiopaque and/or contrast enhancing agents etc. As noted before, it is particularly preferred that the composition at least contains water, such as to yield an aqueous phase having dissolved therein the tonicity agent and, optionally, one or more acidic stress inducing agents with or without buffering agent.

The present composition is preferably presented in the form of a product used in conventional dentistry. In particular the composition may be in the form of a product selected from the group of a filler, an irrigation liquid or a rinsing liquid. In a particularly preferred embodiment of the invention, a composition as defined in any of the foregoing is provided, which has the form of a gel, paste, ointment or a viscous or pseudo-plastic liquid, comprising an aqueous phase as defined herein before, which may be the continuous phase or the dispersed phase. Such composition are particularly suitable as '(temporary) fillers', e.g. during root canal treatment. In another preferred embodiment of the invention, a composition as defined in any of the foregoing is provided, which has the form of a liquid, preferably a solution, emulsion or suspension comprising one or more of the above defined additional ingredients dispersed in the said aqueous phase. Such liquid compositions are particularly suitable for use in dental treatments as irrigation fluid, rinsing liquid or as a drilling or filing fluid. The various formulations referred to herein, as such, are known or will be apparent to those skilled in the art (see, e.g., Remington's Pharmaceutical Sciences, 17th ed., Mack Publishing Co. (1990)). It is therefore apparent to those skilled in the art how to design and prepare suitable compositions within the scope of the invention, on the basis of this description.

As indicated in the foregoing, the compositions of the present invention are suitable and intended for use in dental treatment, typically as a disinfectant or antimicrobial preparation. The term 'dental treatment' in its broadest sense refers to any method of treatment aiming at prevention and/or curing of diseases, disorders and conditions of the soft and hard tissues of the jaw (mandible), the oral cavity, maxillofacial area and the adjacent and associated structures of the human body. As used herein the terms 'disinfectant' and 'antimicrobial' are deemed to be synonymous and are used interchangeable, as referring to the killing of or inhibiting the growth of microorganisms such as bacteria, yeasts and molds (fungi), or protozoans, as well as the destroying viruses. Bacteriocides, antibiotics, germicides and antiseptics are all deemed to constitute specific subclasses of the 'antimicrobials'. Hence, specific embodiments of the present invention provide compositions as defined in the foregoing which are suitable and intended for use as an antiseptic, an antibiotic, an bacteriocidal, a germicidal or a fungicidal preparation.

In accordance with the invention, the compositions are preferably suitable and intended for use in a method of treating and/or preventing apical, lateral or marginal periodontitis, gingivitis, peri-implantitis or other forms of oral infection, preferably for use in a method of treating apical, lateral or marginal periodontitis, gingivitis or other forms of oral infection, most preferably for use in a method of treating apical, lateral or marginal periodontitis. Furthermore, the compositions are preferably suitable and intended for use in endodontic or periodontal treatments, especially in root canal treatment.

Hence in an embodiment, compositions as defined in any of the foregoing are provided, comprising one or more agents that are capable of inducing acidic stress, preferably the sodium salt of an organic acid, for use as a disinfectant or antimicrobial preparation in dental treatment, preferably in endodontic or periodontal treatments, especially in root canal treatment. In another embodiment such compositions are provided for use in a method of treating and/or preventing apical, lateral or marginal periodontitis, gingivitis, peri-implantitis or other forms of oral infection, more preferably for use in a method of treating and/or preventing apical, lateral or marginal periodontitis, gingivitis or other forms of oral infection.

In another embodiment, compositions as defined in any of the foregoing are provided, comprising a tonicity agent in an amount which renders the composition hypertonic, for use as a disinfectant or antimicrobial preparation in endodontic or periodontal treatments or implant surgery, preferably in endodontic or periodontal treatments, especially in root canal treatment. In another embodiment such compositions are provided for use in a method of treating apical, lateral or marginal periodontitis.

A second aspect of the present invention concerns a method of dental treatment, preferably endodontic treatment or periodontal treatment, in a subject, said method comprising the use or application of a composition as defined herein before. As can be inferred from the above, the present method preferably concerns treatment and/or prevention of apical, lateral or marginal periodontitis; treatment and/or prevention of gingivitis; treatment and/or prevention of peri-implantitis; treatment and/or prevention of oral infection. A particularly preferred embodiment of the present invention concerns a method of root canal treatment. As will be understood by those skilled in the art the specific steps performed in a method of treatment of the invention will, in part, depend on the exact aim and nature of the method.

In a first preferred embodiment, a method is provided for treatment and/or prevention of oral infection, including gingivitis, peri-implantitis and periodontitis, wherein the method comprises rinsing the infected dental tissue or the dental tissue at risk of becoming infected, preferably the entire oral cavity, with an amount of a rinsing liquid, comprising a composition as defined in any of the foregoing. Typically, the present method comprises repetitive rinsing, preferably at least two times, more preferably at least three times, most preferably at least 4 times, during treatment. In a particularly preferred embodiment prophylactic treatment is provided wherein the method comprises rinsing dental tissue at risk of becoming infected, preferably the entire oral cavity, at least once every month, more preferably at least once every two weeks, more preferably at least once a week, more preferably at least twice, more preferably at least four times a week, e.g. once or twice daily. It is within the skills of a trained medical professional to determine optimal treatment regimens within the scope of the present invention.

In a second preferred embodiment, a method of root canal treatment is provided, e.g. for treatment of apical or lateral periodontitis, wherein the method comprises the steps of i) mechanically opening and widening of the root canal space and removal of infected pulp from said root canal space; ii) disinfecting the root canal space by irrigation of the root canal space with an irrigation liquid; iii) filling the root canal space with a temporary or permanent filling and iv) temporarily or permanently sealing the opening; wherein a composition as described herein before is used as said irrigation liquid and/or as said temporary root canal filling. In a preferred embodiment, an irrigation liquid and a temporary root canal filling according to the present invention are used. Furthermore, as is known to those skilled in the art, fluids may sometimes be used during the step of mechanically opening and widening of the root canal space, which are herein referred to as 'drilling fluid' or 'filing fluid'. Compositions according to the present invention can also be used for this particular purpose. Using hypertonic fluids of the invention during drilling/filing will reduce the drag of living microorganisms along the root canal during such operation.

In a particularly preferred embodiment of the present method the use of hypertonic liquids or fluids as described above is followed by the use of distilled water (hypotonic). The use of hypertonic and hypotonic liquids and/or fluids may be alternated several times. Without wishing to be bound by any particular theory, it is believed that such alternating uses will even further enhance the disinfecting process because bacteria will adapt to the hypertonic and hypotonic environment. Adaptation takes time and energy and will eventually fail as a result of metabolic exhaustion.

Techniques for treating the pulp canals are known to those of average skill in the art, and the invention is not particularly limited in this regard. Conventional techniques involve the use of hand held rods manufactured of twisted or grinded squared or triangular wires, in the form of reamers or files in a variety of gauges and/or engine driven rotating files or reamers. A variety of techniques for introducing irrigation liquid and/or filler into the root canal space is also available. The instrumented tooth opening may be flushed using a hand held irrigation device, but mechanical automated systems for introducing treatment liquids into the dental pulp chamber and pulp canals are also available. The treatments referred to here above, are as such known or will be apparent to those skilled in the art. It is therefore apparent to those skilled in the art how to practice the invention, on the basis of foregoing.

A third aspect of the present invention concerns a kit, preferably an endodontic or periodontal kit, comprising a first container, ampoule or syringe holding a disinfectant or antimicrobial composition of the present invention, in combination with one or more items selected from the group consisting of endodontic and periodontal bristles, reamers and files; endodontic and periodontal irrigation needles and tips; endodontic and periodontal irrigation syringes; further containers, ampoules and syringes holding an endodontic or periodontic treatment composition selected from root canal fillers, root canal sealers and dental cements; and distributing spirals, e.g. lentulo spirals. The various items referred to here, are as such known or will be apparent to those skilled in the art.

A fourth aspect of the invention concerns the use of a tonicity agent in the manufacture of a medicament for use as a disinfectant or antimicrobial preparation in dental treatment, wherein said disinfectant or antimicrobial preparation comprises an amount of said tonicity agent that renders the medicament hypertonic, in accordance with what has been defined in any of the foregoing.

The following examples further illustrate certain embodiments of the invention, without limiting the scope thereof in any way.

EXAMPLES

Experiment 1

This experiment was performed to establish effectiveness of the compositions (experimental medicament or 'EM') of the present invention, using a 6.2 M NaCl solution, in root canal treatment and to compare its efficiency with calcium hydroxide (CH), which is currently the treatment of choice as already explained in the Background part of this document. Therefore the experimental set-up was to compare the bactericidal effect of EM with CH on a biofilm of *Enterococcus faecalis* and *Pseudomonas aeruginosa*.
Materials and Methods The biofilm model used here was recently described by Deng et al. 2009. In brief, round glass cover slips attached to a custom made stainless steel lid, were suspended in medium inoculated with bacteria. In this model biofilm growth is an active process against gravity.

A dual-species biofilm was used because of its increased resistance to antimicrobials (Özok et al. 2007, Kara et al. 2007, Adrião et al. 2008). *E. faecalis* was chosen as the test organism because the reported association with persistent periapical pathosis (Sundqvist et al. 1998, Siqueira & Rocas 2004, Stuart et al. 2006). Factors facilitating its presence in filled root canals with persistent lesions include the ability to invade dentinal tubules (Haapasalo & Ørstavik 1987, Weiger et al. 2002), to tolerate the alkaline pH of $Ca(OH)_2$ (Evans et al. 2002, Nakajo et al. 2006), to withstand long periods of starvation with subsequent recovery in the presence of serum (Figdor et al. 2003), to survive for a long period in the root canal without additional nutrients (Sedgley et al. 2005) and to easily grow in a laboratory setting. Furthermore, *E. faecalis* is known to efficiently accumulate the compatible solutes from the medium to counteract increased osmotic pressure (Pichereau et al. 1999). *P. aeruginosa* is an aerobic gram negative motile rod, infamous for its excellent alginate producing property. No matter how smooth a surface, *P. aeruginosa* adheres within 30 sec (Vanhaecke et al. 1990). Although classified as aerobic, *P. aeruginosa* survives anaerobic conditions (Yoon et al. 2002). Its presence in the root canal is associated with failed endodontic treatment (Ranta et al. 1988, Sirén et al. 1997).
Microbiology Cells of *E. faecalis* V583 and *P. aeruginosa*, both clinical isolates, were grown and maintained as pure cultures on blood agar plates. *E. faecalis* was grown under anaerobic conditions (80% $N_2$, 10% $H_2$ and 1.0% $CO_2$) while *P. aeruginosa* was grown in air, both at 37° C. Because of their shape, Gram-staining and atmospheric preferences, distinguishing between the two species with (ISM and CFU was fairly simple. Growth media for overnight cultures and biofilms were Brain Heart Infusion Broth (BHI, Oxoid, Basinstoke, UK) and BHI-broth contained 0.5 BHI, 50 mM pipes, 5% saccharose, 1 mM $Ca^{2+}$ during biofilm growth. In the experimental phase, sodium chloride (NaCl), (Merck, Darmstadt, Germany) was added to the BHI-broth to raise the osmotic value. Other medicaments used were saturated $Ca(OH)$ in BHI-broth (slurry), 2% sodium hypochlorite (NaOCl), Merck, Darmstadt, Germany), 2% sodium thiosulphate (STS) in peptone water (1% peptone (Oxoid) in water) for neutralising the NaOCl. Phosphate buffered saline (PBS, Oxoid) was used to wash the negative controls, as a neutralising agent for NaCl, $Ca(OH)_2$ and for serial
Biofilm Growth Fresh cultures of each micro-organism were obtained by suspending one loopful bacteria in 5 mL BHI and grown overnight at 37° C. in air. Numbers of CFU were estimated by optical density measurement at 600 nm and relating the readings to previously performed bacterial counts. 100 µL with approximately $2\times10^9$ *E. faecalis* and 100 µL with approximately $2\times10^7$ *P. aeruginosa* were inoculated in wells of a 24 Well Multiwell Plate (Greiner Bio-one, Frickenhausen, Germany) containing 1.5 mL BHI-broth. Round glass cover slips (MMG, Germany), diameter 15 mm, mounted in a custom-made stainless steel lid, were suspended in the BHI-broth. Biofilms were grown on glass cover slips to be able to monitor the biofilm growth with a confocal laser scanning microscope (CLSM; Leica SP2-OBS). The biofilms were firmly attached on the glass slips, allowing manipulation of the coverslips without biofilm disruption.

Biofilms were grown on the coverslips for 96 h before exposure to the medicaments. After 6-h growth the biomass in a biofilm increases while the quantity of living cells is more or less established (Wilson et al. 1996). The broth was refreshed daily. Inoculation of bacteria and the biofilm growth took place at 37° C. in air. After 48 h biofilm growth was confirmed with the aid of CLSM. Three coverslips with attached biofilms were viewed with CLSM after staining with Syto 9 and propidium iodine (PI) (LIVE/DEAD® BacLight™) according to the manufacturer's instruction. Intact, live cells stain fluorescent green, while dead cells with damaged plasma membranes stain fluorescent red. Later on biofilm growth was confirmed clinically.

Experiments

After 96 h the coverslips with the attached bio films were submerged in NaCl-broth or $Ca(OH)_2$-broth for 4 h, 24 h, 48 h, 72 h and 168 h. The negative controls were kept in BHI-broth. Where applicable, the incubation fluids were refreshed daily. Submersion in NaOCl 2% for 10 min served as a positive control. After the experiments, the coverslips were removed from the lid and submerged in copious quantities of neutralising agents: 10 minutes PBS for the NaCl-groups, $Ca(OH)_2$ groups and negative controls and 30 minutes in STS for the positive controls. Bacterial cells were harvested using a sterile cotton swab and re-suspended in 1 mL of PBS by vigorously moving the cotton swab up and down fifty times in an 1.5 mL test tube (Eppendorf, Standard Micro Test Tube 3810). The suspension was serially diluted and plated on blood-agar plates for total viable count determination (CFU). The CFU morphologies of E. faecalis and P. aeruginosa resemble each other when grown in air, but when incubated in the absence of oxygen CFU of P. aeruginosa had a distinct different morphology compared with E. faecalis. Colonies were very small. Therefore the plates were incubated anaerobically for 48 h at 37° C. CFU of both E. faecalis (large white colonies) and P. aeruginosa (small dark colonies) were determined. Then the plates were incubated for another 24 h in air to confirm the presence or absence of P. aeruginosa (large yellowish-green colonies). Each group consisted of three specimens and each experiment was performed in triplicate.

Confocal Laser Scanning Microscopy (CLSM) Analysis

For imaging a Leica DM-IRB inverted microscope/SP2-AOBS confocal system was used. Images (512*512 pixels) were acquired with a 40×/NA 1.25 HCX PL APO oil objective. The final pixel size was 0.776 µm. The pinhole size was set at 1 Airy, resulting in a Z resolution of approximately 0.5 µm. Image stacks were acquired with a stepsize of 0.3 µm. Excitation/detection of Syto-9 and propidium iodide (PI) was done simultaneously with 488 nm excitation and with 500-550 nm detection for SYTO 9 and 600-690 nm detection for PI respectively. Using gain and offset of the photo multiplying tube, the images were adapted to the full (8 bit) dynamic range of the system. An overlay of the 2 images (green and red) was generated with the Leica software.

Statistical Analysis

CFU counts were logarithmically transformed. Data were analysed by one-way analysis of variance (ANOVA) to compare the experimental groups to the negative controls. The significance level was set at $\alpha=0.05$. The analyses were carried out with the statistical package SPSS version 12 (SPSS Inc. Chicago, Ill., USA).

Results:

Microbiology

The results are presented as log CFU reduction per biofilm compared with the controls (FIG. 1). The controls contained 8.1±0.6 log (CFU) microorganisms per biofilm, which gradually increased in time.

The mean log reduction of CFU in the NaCl groups for both E. faecalis and P. aeruginosa after 72 h and after 168 h was 6 and 8 respectively, and was statistically significant compared to the controls. At 168 h the control biofilms contained on average $1.5\times10^9$ CFU P. aeruginosa, of which none could be detected after 168 h of NaCl. E. faecalis was reduced to a mean of 40 CFU. The reductions were highly significant for both species (P<0.001) and showed a significant linear trend in time.

$Ca(OH)_2$ reduced P. aeruginosa significantly, (P=0.02), however, the reduction did not increase with an increased application time. Reduction of E. faecalis by $Ca(OH)_2$ was not significant (P=0.09). After 72 h a log 2 reduction was determined for both species, but after 168 h bacterial growth recovered until a mean log 1 reduction.

The NaOCl groups showed 100% kill after 10 min exposure.

With visual observation the glass coverslips exposed to NaCl showed no signs of a biofilm plaque after the experimental phase. Calcification of the plaque was an unexpected observation in the $Ca(OH)_2$ group. After 24 h all samples showed bio film calcification. The thickness of the plaque increased during the experiment. The calcified plaque was firmly attached to the coverslip and could not be removed completely by rubbing with a cotton swab.

Confocal Laser Scanning Microscopy (CLSM)

The control bio films showed masses of live and dead cells embedded in an amorphous mass.

NaCl influenced the growth pattern of persisting bacterial cells. No amorphous biomass was visible, with visual observation as well as on CLSM-images. Since the coverslip of the NaCl-group contained almost no bacteria, we examined the cover slips with a higher magnification to find left-over cells.

$Ca(OH)_2$ had an effect on the growth pattern of the biofilm. Bacterial cells formed clusters. This is clearly visible in a cross-section of the same sample.

Discussion:

In this biofilm model NaCl reduced the bacterial load significantly more than the $Ca(OH)_2$ (FIG. 1). Micro-organisms counteract the reduction of water activity due to the extracellular hyperosmotic value, by restoring the intracellular solute concentration through the uptake or synthesis of small ions and molecules, which do not interfere with its metabolism (Csonka 1989, Guttierez et al. 1995, Record et al. 1998). Whether an environment with low water activity is lethal, depends also partly on the ability of the micro-organisms to adjust to these changes and on the availability of compatible solutes within their reach. Low hypertonic concentrations of NaCl are sufficient to kill bacteria in a medium low in compatible solutes (Lee et al. 1972, Faklam et al. 1973, Pichereau et a/0.1999, Bautista et al. 2008). It is likely, that undebrided areas of the root canal system are packed with nutrients, giving the micro-organisms opportunities to counteract the environmental change. In this study the undebrided root canal was mimicked by growing the bio films in BHI-broth with added NaCl or $Ca(OH)_2$. Providing nutrients also prevented bacterial death as a result of starvation.

Storing and synthesising compatible solutes are energy-demanding processes. Once the stocks of compatible solutes or energy resources are depleted, bacteria enter the stationary phase, where eventually bacterial death follows (Csonka & Hanson 1991). The phenomenon osmosis is solely dependent on the concentration of solutes. The attraction of solvents by the solutes continues until a certain equilibrium has been reached. Therefore, some effect may be expected lateral of the main root canal.

It was remarkable that after the exposure to NaCl the mucous growth (biofilm) on the coverslips had disappeared and therefore, with visual observation the coverslips were 'cleaner' than the negative controls and the calcium hydroxide group. Removal of the amorphous mass was confirmed with the CLSM-images. Apparently the NaCl had some effect on the structure of the biofilm matrix. Also the extracellular polymeric saccharides formation essential for biofilm growth, could have been disturbed by the presence of NaCl. It is common knowledge that inhalation of physiologic saline helps to clear an obstructed nose or nasal sinuses. Looking for an explanation the literature was searched. Reverse osmosis membranes are used in advanced wastewater reclamation for the production of clean water. A major challenge in this industry is cleaning of the membranes, which are fouled by the considerable amount of organic debris in wastewater. The fouling substance on the membranes cannot be removed using sole irrigants. Cleaning of the membranes involves both physical and chemical cleaning; physical removal of the bulk foulants followed by chemical disinfection (Ang et al. 2006). It was discovered that exposure of the fouled membranes to a NaCl-solution resulted in disruption and removal of the fouling layer (Lee & Elimelech 2007). In this study the term biofilm was not mentioned, but the contaminating layer was addressed to as fouling. The authors used alginates in their experiments to imitate the fouling. The results found in this study cannot be extrapolated to the situation in the root canal system, but the study may shed a light on the cleaning effect of NaCl.

$Ca(OH)_2$ is world-wide the most used intra-canal medicament. The antimicrobial property of $Ca(OH)_2$ in root canals was first tested by Byström and colleagues (1985). Bacterial counts were reduced. These observations were confirmed in 1991 by Sjögren and co-workers. After the application of $Ca(OH)_2$ for a week in infected root canals, no bacteria were retrieved or cultivated, suggesting that $Ca(OH)_2$ rendered the root canals free of cultivable bacteria. However, it has to be kept in mind that the clinical sampling of the root canals was done with the paper point technique. It is nowadays generally accepted that this technique has many draw-backs mainly because the paper point can never reach the entire root canal wall, lateral canals and the places where the micro-organisms can harbour which survived the chemo-mechanical cleaning procedures. The paper point sampling technique gives a good indication of what can be removed from the root canal not what is still left (Sathorn et al. 2007$^a$). Furthermore, microorganisms in the starvation phase are impossible to culture or detect. Based on the current best available evidence, calcium hydroxide has limited effectiveness in eliminating bacteria from human root canal when assessed by culture techniques (Peters et al. 2002, Waltimo et al. 2005, Sathorn et al. 2007$^b$). Calcium hydroxide has some antibacterial efficacy on planktonic bacteria (Stuart et al. 1991, Georgopoulou et al. 1993, Ferreira et al. 2007), microorganisms however reside in the root canal system in a biofilm configuration (Chávez de Paz 2007$^a$). Studies on the effect of $Ca(OH)_2$ on biofilms show that E. faecalis in a biofilm is resistant to $Ca(OH)_2$ (Abdullah et al. 2005, Chávez et al. 2007$^b$). The precise mode of action of $Ca(OH)_2$ on micro-organisms has not been fully elucidated (Siqueira & Lopes 1999). Clinical outcome studies comparing single-visit treatment to multi-visits treatment with medication of $Ca(OH)_2$ show no significant differences in healing between groups (Weiger et al. 2000, Peters et al. 2002, Sathorn et al. 2005, Molander et al. 2007). Besides the questionable antimicrobial effect, there are more draw-backs to the use of $Ca(OH)_2$. Calcification of the biofilm is an unwanted side-effect of $Ca(OH)_2$ and severely hampers thorough disinfection. CLSM images showed viable bacterial aggregates embedded in a calcified matrix. The calcification of an E. faecalis biofilm on dentine has been shown (Kishen et al. 2006).

Calcium hydroxide is weakly bactericidal (Nakajo et al. 2006) possibly provoking a shift in the endodontic flora towards more resistant species. Some bacterial species produce more extracellular polysaccharides when $Ca^{2+}$ is available (Lattner et al. 2003, Sarkisova et al. 2005). During the pilot of this study, CLSM-images revealed formation of viable E. faecalis-aggregates on the coverslips when 1 mM $Ca^{2+}$ was added to the broth, while in broth without calcium, E. faecalis did not adhere. These findings may make the use of $Ca(OH)_2$ as an innocent inter-visit space-maintainer questionable, but this needs further investigation.

Conclusions:

In this model E. faecalis and P. aeruginosa produced a reproducible and stable dual-species biofilm. A hypertonic saline solution is able to kill in a biofilm, micro-organisms representative for the flora of an infected root canal and is therefore suitable for use as root canal disinfectant. Calcium hydroxide was not effective in this model.

Experiment 2

Weak acids have a pKa below 5. Weak acid stress can only be induced if the protonated, uncharged form of the acid diffuses into the cell. Therefore the pH of the medicament must be lower than the cellular pH. With a low pH, below 5.5, a lesser concentration of acid is needed than at a higher pH, where for the same efficacy the concentration must increase. But at pH 5.7 demineralization of dentin and enamel occurs.

A 6.2 M NaCl in broth solution proved to be bactericidal on a dual species biofilm. $10^8$ and $10^7$ reductions were reached after a week's exposure, resulting in eradication of one species (Experiment 1). It is assumed that a higher concentration of a hygroscopic salt will be more bactericidal resulting in quicker and more reliable eradication of all species, including E. faecalis. By imposing the bacteria with another added stress factor the efficacy will increase.

This leads to the development of an EM with a higher molarity and the development of an EM that provokes additional weak acid stress within the micro-organisms, or both. Already identified compounds, mentioned in various preferred embodiments will be screened on efficacy in the same bio film model used in the preliminary study.

Materials and Methods

Dual-species biofilms of Enterococcus faecalis and Pseudomonas aeruginosa are cultivated on glass coverslips suspended in bacterial inoculate. Biofilms are cultured for 24 h. The coverslips with attached biofilms are submersed in the experimental compounds during 4 h, 24 h, 48 h. Two percent sodium hypochlorite and BHI-broth serve as positive and negative controls. After rinsing in physiologic saline (PBS) the bacterial cells are harvested from the coverslips and re-suspended in PBS, serially diluted, plated on blood-agar plates and incubated anaerobically for 48 h and in air for 24 h at 37° C. The bactericidal effects are assessed by determining the colony forming units.

Sodium iodide, magnesion chloride and mannitol (high osmotic value) and sodium lactate, sodium acetate, sodium sorbate and sodium formate (combination of osmotic and weak acid stress) are tested.

Experiment 3

The purpose of this study is to investigate whether dentine has an inhibitory effect on the mode of action of the EM.

The antimicrobial efficacy of irrigating solutions and local disinfectants used in endodontics appears to be poorer in vivo than in vitro. There are several reasons for the lower in vivo performance, but clearly inactivation of the disinfectants by dentin and other substances present in the necrotic root canal is one factor contributing to the recognized difficulty in completely eradicating micro-organisms from the root canal system. Dentin chips have a buffering capacity in in vitro studies when added to the test tubes with microbes and antimicrobials. In this in vitro study overnight cultures of E. faecalis are exposed to the medicament with and without added dentin chips. After 24 h of incubation serial tenfold dilutions are made and cultured on bloodagar plates. The colonies are counted.

This leads to confirmation of the activity of the different embodiments of the EM and optimal buffering of the different embodiments of the EM.

Experiment 4

Resazurin Metabolism Assay for Screening Compounds to be Used as Root Canal Disinfectants on an *Enterococcus faecalis* Biofilm After non surgical root canal treatment, microorganisms, grouped in a biofilm, can still be detected in distant anatomic sites like isthmuses. Biofilm is a loose definition of microbial aggregates that usually accumulate at a solid-liquid interface and are encased in a matrix of highly hydrated extracellular polymeric substances (EPS). Microorganismal cells exist within and are surrounded with this self-produced matrix of EPS and consequently, are less susceptible to antimicrobial actions like for instance antibiotics.

The purpose of the study is to select the most efficacious compound with its most effective concentration and pH inhibiting the metabolism of a single-species biofilm of *Enterococcus faecalis*. Several compounds are selected of which the saturated solution has a higher molarity than sodium chloride or which combine high solubility with weak acid stress action. To confirm antibiofilm action these compounds are screened in a biofilm model.

In biofilm research viability testing, using colony-forming unit (CFU) counts is frequently applied. This method is laborious, time consuming, and not suitable for high-throughput screening. Moreover, biofilms have to be efficiently removed from the surface and dispersed before plating, and the efficacy of this process is often in question. Simpler methods (eg, fluorescence live/dead cell staining and metabolic activity indicators) have previously been suggested because they could be high throughput and avoid the biofilm detachment/ dispersal steps.

Resazurin is one of the common metabolic activity indicators. It is a nontoxic, water-soluble dye (blue and nonfluorescent) that can be reduced to water-soluble resorufin (pink and highly fluorescent) by metabolically active bacteria. It has been used to assess planktonic bacterial viability, adaptation to stress, and bacterial contamination. Recently, it was also explored for its potential of biofilm quantification in microtiter plates, and from six assays tested, it was suggested as one of the best alternatives for CFU counts. It was also successfully used to evaluate disinfection efficacy on single-species biofilms of several clinically relevant (nonoral) pathogenic bacteria.

Materials and Methods

Clinical *E. faecalis* strain E2 (kindly given by Dr C. M. Sedgley) (22) was used in this study. The strain was routinely grown anaerobically on blood agar at 37° C. Biofilms were grown in modified semidefined biofilm medium (BM) as described previously (17). The pH of this medium was 7.0.

Biofilms were grown in an active attachment Calgary biofilm model. This model consists of a standard 96-well microtiter plate and a lid with an identical number of polystyrene pegs that fit into the wells (Nunc™, Roskilde, Denmark) (23, 24). It was chosen to avoid potential bacterial sedimentation in the flat-bottom 96-well microtiter plate but to keep the 96-well high-throughput advantage for disinfection treatment assays.

Overnight culture of *E. faecalis* was diluted to approximately $1.2 \cdot 10^8$ cells/mL in BM medium with addition of sucrose 0.2%. Two hundred µL of the cell suspension was dispensed into a sterile 96-well plate. The plate was then covered with a sterile lid containing 96 pegs. After 8 hours of incubation, the pegs were placed in fresh BM (with 0.2% sucrose). After another 16 hours of incubation, the pegs with adhered biofilms were transferred to a 96-well plate with the compounds to be tested. Biofilms were treated for 15 min, 1 or 2 hours after which the treatments were stopped by immersing the bio film pegs in neutralizer (buffered peptone water with 1% sodium thiosulfate) for 5 minutes (18). The treatment control group was also subjected to the neutralizer incubation after which the bio films were washed three times in phosphate buffered saline (PBS). Subsequently the pegs were immersed in 0.016 mg/mL resazurin in BM medium with sucrose 0.2% (BMS) and incubated at 37° C.

The fluorescence intensity (FI) of each well was recorded at room temperature in a fluorimeter (Spectramax M2; Molecular Device, Sunnyvale, Calif.) using the fluorescence setting with 485-nm excitation and 580-nm emission wavelength. Readings were taken at 10 minutes and 3 hours.

For one experiment, one and a half 96-well plates were needed to test the compounds in various concentrations with pH 6 or 7. Control groups were biofilms kept in BMS, biofilms kept in PBS, negative controls and biofilms treated with sodium hypochlorite 2% as positive control group. The rest of the wells were used for sterility controls.

The tested compounds were selected based on their high solubility, non-toxicity and weak acid behaviour. In this assay were tested: sodium formate, sodium acetate, sodium lactate and potassium sorbate. Sodium chloride was also included to compare its efficacy, based on osmotic stress alone, to the compounds with both osmotic and weak acid stress.

In a series of cascade experiments, compounds or concentrations proving to be unsatisfactory were sequentially eliminated.

Evaluation on Treatment Efficacy

Figure 2:
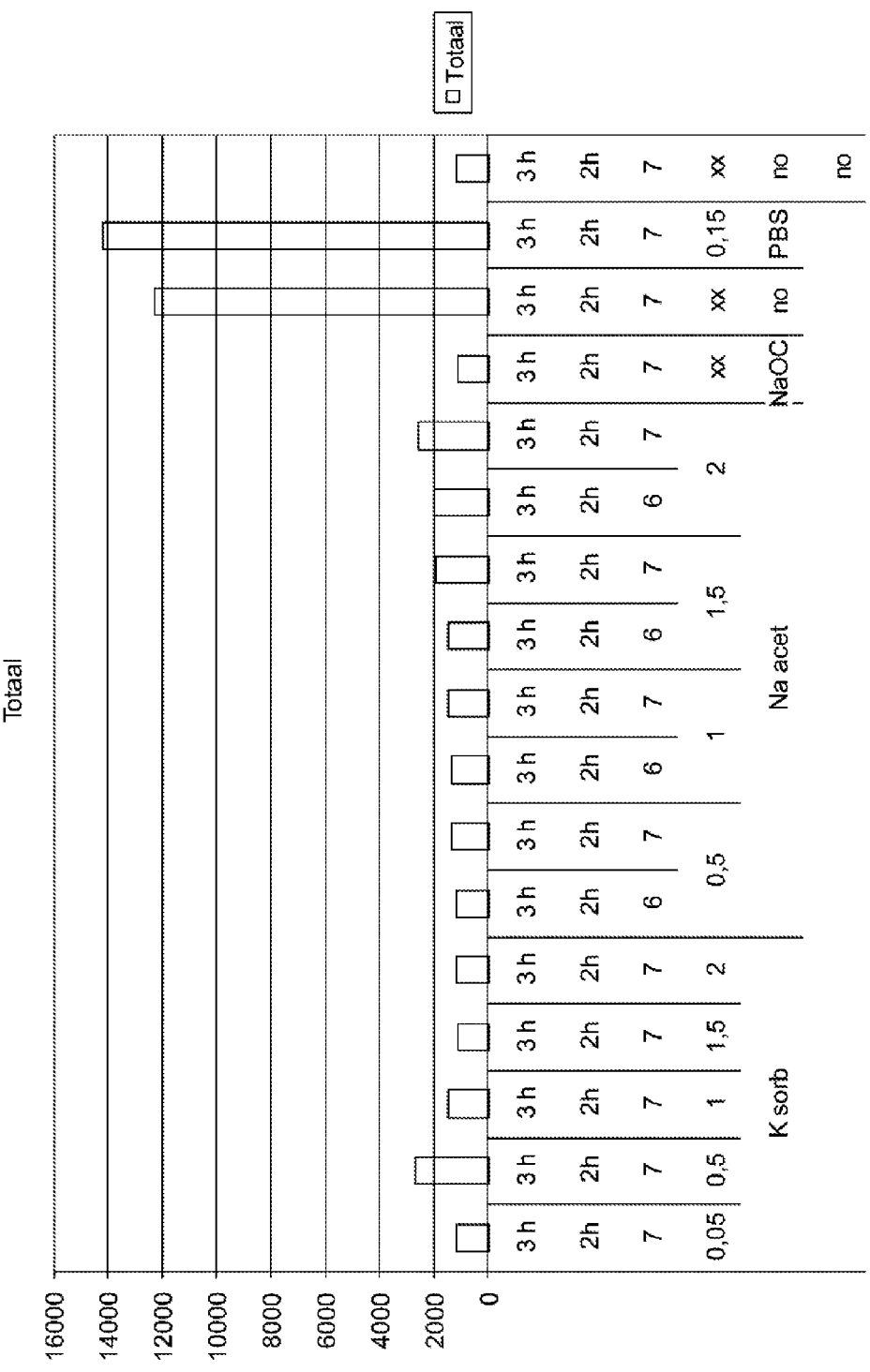
FIG. 2: Fluorescence readings of Resazurin assay of biofilms that were treated for 2 hours with potassium sorbate 0.05 M, 0.5 M, 1 M, 1.5 M, 2 M (pH 7), Sodium acetate 0.5 M, 1 M, 1.5 M, 2 M (pH 6 or 7). NaOCl served as positive control, PBS and no treatment were negative controls. Last column represents the sterility control. Readings were taken after 3 hours

Resazurin Metabolism Assay. Resazurin can be used as a metabolic activity indicator for *E. faecalis* as has recently been established by Jiang et al. 2011. When evaluating the metabolism of the biofilms after treatment, the biofilms were incubated at 37° C. in BMS with added resazurin stock solution to achieve a final concentration of 0.0016%. After 10 minutes (baseline) or 3 hours (just before the peak reading) FI readings were taken. This experiment was performed in quadruplicate and repeated twice. For all FI readings, a background control group in which 0.0016% resazurin was mixed with sterile BMS was included to record background FI changes, which were subsequently subtracted from the FI of each well. Treatment efficacy was calculated as the percentage reduction in FI values after treatment relative to the values in the control group. The results are presented in FIG. 2.

REFERENCES

Abdullah M, Ng Y L, Gulabivala K, Moles D R, Spratt D A (2005) Susceptibilties of two *Enterococcus faecalis* phenotypes to root canal medications. *Journal of Endodontics* 31, 30-6.

Adrião A, Vieira M, Fernandes I, Barbosa M, Sol M, Tenreiro R P, Chambel L, Barata B, Zilhao I, Shama G, Perni S, Jordan S J, Andrew P W, Faleiro M L (2008) Marked intra-strain variation in response of *Listeria monocytogenes* dairy isolates to acid or salt stress and the effect of acid or salt adaptation on adherence to abiotic surfaces. *International Journal of Food Microbiology* 31, 142-50.

Ang W S, Lee S, Elimelech M (2006) Chemical and physical aspects of cleaning of organic-fouled reverse osmosis membranes. *Journal of Membrane Science* 272, 198-210.

Bautista-Gallego J, Arroyo-López F N, Durán-Quintana M C, Gamido-Fernández A (2008) Individual Effects of Sodium, Potassium, Calcium, and Magnesium Chloride Salts on *Lactobacillus pentosus* and *Saccharomyces cerevisiae* Growth. *Journal of Food Protection* 71, 1412-21.

Byström A, Claesson R, Sundqvist G (1985) The antibacterial effect of camphorated paramonochlorophenol, camphorated phenol and calcium hydroxide in the treatment of infected root canals. *Endodontic & Dental Traumatology* 1, 170-5.

Chávez de Paz L E (2007$^a$) Redefining the persistent infection in root canals: possible role of biofilm communities. *Journal of Endodontics* 33, 652-62.

Chávez de Paz L, Bergenholtz G, Dahlen G, Svensater G (2007$^b$) Response to alkaline stress by root canal bacteria in biofilms. *International Endodontic Journal* 40, 344-55.

Costerton J W, Lewandowski Z, Caldwell D E, Korber D R, Lappin-Scott H M (1995) Microbial Biofilms. *Annual Reviews Microbiology* 49, 711-45.

Csonka L N (1989) Physiological and Genetic Responses of Bacteria to Osmotic Stress. *Microbiological Reviews* 53, 121-47.

Csonka L N, Hanson A D (1991) Prokaryotic osmoregulation: genetics and physiology. *Annual Review of Microbiology* 45, 569-606.

Deng D M, Hoogenkamp M A, Exterkate A M, Jiang L M, Van der Sluis L W M, Ten Cate J M, Crielaard W M (2009) Influence of *Streptococcus mutans* on *Enterococcus faecalis* Biofilm Formation. *Journal of Endodontics* 35, 1249-52.

Estrela C, Bueno M R, Leles C R, Azevedo B, Azevedo J R. Accuracy of cone beam computed tomography and panoramic periapical radiography for detection of apical periodontitis. *J Endod* 2008; 34: 273-279

Evans M, Davies J K, Sundqvist G, Figdor D (2002) Mechanisms involved in the resistance of *Enterococcus faecalis* to calcium hydroxide. *International Endodontic Journal* 35, 221-8.

Faklam R R (1973) Comparison of Several Laboratory Media for Presumptive Identification of Enterococci and Group D Streptococci. *Applied Microbiology* 26, 138-45.

Fan B, Cheung G S, Fan M, Gutmann J L, Bian Z (2004) C-shaped canal system in mandibular second molars: Part I—Anatomical features. *Journal of Endodontics* 30, 899-903.

Ferreira F B, Torres S A, Rosa O P, Ferreira C M, Garcia R B, Marcucci M C, Gomes B P (2007) Antimicrobial effect of propolis and other substances against selected endodontic pathogens. *Oral Surgery, Oral Medicine, Oral Pathology, Oral Radiology and Endodontology* 104, 709-16.

Figdor D, Davies J K, Sundqvist G (2003) Starvation survival, growth and recovery of *Enterococcus faecalis* in human serum. *Oral Microbiology and Immunology* 18, 234-9.

Georgopoulou M, Kontakiotis E, Nakou M (1993) In vitro evaluation of the effectiveness of calcium hydroxide and paramonochlorophenol on anaerobic bacteria from the root canal. *Endodontic & Dental Traumatology* 9, 249-253.

Gutierrez C, Abee T, Booth I R (1995) Physiology of the osmotic stress response in microorganisms. *International Journal of Food Microbiology* 28, 233-44.

Haapasalo M, Ørstavik D (1987) In vitro Infection and disinfection of dentinal tubules. *Journal of Dental Research* 66, 1375-9.

Kakehashi S, Stanley H R, Fitzgerald R J (1965) The effects of surgical exposures of dental pulps in germ-free and conventional laboratory rats. *Oral Surgery, Oral Medicine and Oral Pathology* 20, 340-9.

Kara D, Luppens S B, van Marle J, Özok R, ten Cate J M (2007) Microstructural differences between single-species and dual-species biofilms of *Streptococcus mutans* and *Veillonella parvula*, before and after exposure to chlorhexidine. *FEMS Microbiology Letters* 271, 90-7.

Kishen A, George S, Kumar R (2006) *Enterococcus faecalis*-mediated biomineralized biofilm formation on root canal dentine in vitro. *Journal of Biomedical Materials Research Part A* 77, 406-15.

Lattner D, Flemming H C, Mayer C (2003) 13C-NMR study of the interaction of bacterial alginate with bivalent cations. *International Journal of Biological Macromolecules* 33, 81-8.

Lee W S (1972) Improved Procedure for Identification of Group D Enterococci with Two New Media. *Applied Microbiology* 24, 1-3.

Lee S, Elimelech M (2007) Salt Cleaning of organic-fouled reverse osmosis membranes. *Water Research* 41, 1134-42.

Lin L M, Skribner J E, Gaengler P (1992) Factors associated with endodontic treatment failures. *Journal of Endodontics* 18, 625-7.

Molander A, Reit C, Dahlen G, Kvist T (1998) Microbial status of root-filled teeth with apical periodontitis. *International Endodontic Journal* 31, 1-7.

Molander A, Warfvinge J, Reit C, Kvist T (2007) Clinical and radiographic evaluation of one- and two-visit endodontic treatment of asymptomatic necrotic teeth with apical periodontitis: a randomized clinical trial. *Journal of Endodontics* 33, 1145-8.

Morfis A, Sylaras S N, Georgopoulou M, Kernani M, Prountzos F (1994) Study of the apices of human permanent teeth with the use of a scanning electron microscope. *Oral Surgery, Oral Medicine and Oral Pathology* 77, 172-6.

Nair P N, Henry S, Cano V (2005) Microbial status of apical root canal system of human mandibular first molars with primary apical periodontitis after 'one-visit' endodontic treatment. *Oral Surgery, Oral Medicine, Oral Pathology, Oral Radiology and Endodontics* 99, 231-52.

Nakajo K, Komori R, Ishikawa S, Ueno T, Suzuki Y, Iwami Y, Takahashi N (2006) Resistance to acidic and alkaline environments in the endodontic pathogen *Enterococcus faecalis*. *Oral Microbiology and Immunology* 21, 283-8.

Özok A R, Wu M K, Luppens S B, Wesselink P R (2007) Comparison of growth and susceptibility to sodium hypochlorite of mono- and dual-species biofilms of *Fusobacterium nucleatum* and *Peptostreptococcus* (*micromonas*) *micros*. *Journal of Endodontics* 33, 819-22.

Peters L B, Van Winkelhoff A J, Buijs J F, Wesselink P R (2002) Effects of intrumentation, irrigation and dressing with calcium hydroxide on infection in pulpless teeth with periapical bone lesions. *International Endodontic Journal* 35, 13-21.

Pichereau V Bourot S, Flahaut S, Blanco C, Auffray Y, Bernard T (1999) The osmoprotectant glycine betaine inhibits salt-induced cross-tolerance towards lethal treatment in *Enterococcus faecalis*. *Microbiology* 145, 427-35.

Portenier I, Waltimo T, Ørstavik D, Haapasalo M (2005) The Susceptibility of Starved, Stationary Phase, and Growing Cells of *Enterococcus faecalis* to Endodontic Medicaments. *Journal of Endodontics* 31, 380-6.

Ranta K, Haapasalo M, Ranta H (1988) Monoinfection of root canal with *Pseudomonas aeruginosa*. *Endodontics & Dental Traumatology* 4, 269-72.

Record M T Jr, Courtenay E S, Cayley D S, Guttman H J (1998) Responses of *E. coli* to osmotic stress: large changes in amounts of cytoplasmic solutes and water. *Trends in Biochemical Sciences* 23, 143-8.

Sarkisova S, Patrauchan M A, Berglund D, Nivens D E, Franklin M J (2005) Calcium-induced virulence factors associated with the extracellular matrix of mucoid *Pseudomonas aeruginosa* biofilms. *Journal of Bacteriology* 187, 4327-37.

Sathorn C, Parashos P, Messer H H (2005) Effectiveness of single-versus multiple-visit endodontic treatment of teeth with apical periodontitis: a systematic review and meta-analysis. *International Endodontic Journal* 38, 347-55.

Sathorn C, Parashos P, Messer H H (2007[a]) How useful is root canal culturing in predicting treatment outcome? *Journal of Endodontics* 33, 220-5.

Sathorn C, Parashos P, Messer H H (2007[b]) Antibacterial efficacy of calcium hydroxide intracanal dressing: a systematic review and meta-analysis. *International Endodontic Journal* 40, 2-10.

Sedgley C M, Lennan S L, Appelbe O K (2005) Survival of *Enterococcus faecalis* in root canals ex vivo. *International Endodontic Journal* 38, 735-42.

Seltzer S, Bender I B, Smith J, Freedman I, Nazimov H (1967) Endodontic failures—an analysis bases on clinical, roentgenographic, and histologic findings I & II *Oral Surgery, Oral Medicine and Oral Pathology* 23, 500-30.

Siqueira J F Jr, Lopes H P (1999) Mechanisms of antimicrobial activity of calcium hydroxide: a critical review. *International Endodontic Journal* 32, 361-9.

Siqueira J F Jr, Rocas I N (2004) Polymerase chain reaction-based analysis of microorganisms associated with failed endodontic treatment. *Oral Surgery, Oral Medicine, Oral Pathology, Oral Radiology and Endodontology* 97, 85-94.

Sirén E K, Haapasalo M P, Ranta K, Salmi P, Kerosuo E N (1997) Microbiological findings and clinical treatment procedures in endodontic cases selected for microbiological investigations. *International Endodontic Journal* 30, 91-5.

Sjögren U, Figdor D, Spangberg L, Sundqvist G (1991) The antimicrobial effect of calcium hydroxide as a short-term intracanal dressing. *International Endodontic Journal* 24, 119-25.

Sperber W H (1983) Influence of water activity on foodborne bacteria—a review. *Journal of Food Protection* 46, 142-50.

Stuart K G, Miller C H, Brown C E Jr, Newton C W (1991) The comparative antimicrobial effect of calcium hydroxide. *Oral Surgery, Oral Medicine and Oral Pathology* 72, 101-4.

Stuart C H, Schwartz S A, Beeson T J, Owatz C B (2006) *Enterococcus faecalis*: Its Role in Root Canal Treatment Failure an Current Concepts in Retreatment. *Journal of Endodontics* 32, 93-8.

Sundqvist G, Figdor D, Persson S, Sjögren U (1998) Microbiologic analysis of teeth with failed endodontic treatment and the outcome of conservative re-treatment. *Oral Surgery, Oral Medicine, Oral Pathology, Oral Radiology and Endodontology* 85, 86-93.

Vanhaecke E, Remon J P, Moors M, Raes F, De Rudder D, Van Peteghem A (1990) Kinetics of *Pseudomonas aeruginosa* Adhesion to 304 and 316-L Stainless Steel: Role of Cell Surface Hydrophobicity. *Applied Environmental Microbiology* 56, 788-95.

Vertucci F J (1984) Root canal anatomy of the human permanent teeth. *Oral Surgery, Oral Medicine and Oral Pathology* 58, 589-99.

Waltimo R, Trope M, Haapasalo M, Ørstavik D (2005) Clinical Efficacy of Treatment Procedures in Endodontic Infection Control and One Year Follow-Up of Periapical Healing. *Journal of Endodontics* 31, 863-6.

Watnick P, Kolter R (2000) Biofilm, City of Microbes. *Journal of Bacteriology* 182, 2675-9.

Weiger R, Rosendahl R. Löst C (2000) Influence of calcium hydroxide intracanal dressing on the prognosis of teeth with endodontically induced periapical lesions. *International Endodontic Journal* 33, 219-26.

Weiger R, de Lucena J, Decker H E, Löst C (2002) Vitality status of microorganisms in infected human root dentine. *International Endodontic Journal* 35, 166-71.

Wilson M, Patel H, Fletcher J (1996) Susceptibility of biofilms of *Streptococcus sanguis* to chlorhexidine gluconate and cetylpyridinium chloride. *Oral Microbiology and Immunology* 11, 118-92.

Wu M K, R'oris A, Barkis D, Wesselink P R (2000) Prevalence and extent of long oval canals in the apical third. *Oral Surgery, Oral Medicine, Oral Pathology, Oral Radiology and Endodontology* 89, 739-43.

Wijnker J J, Koop G, Lipman L J A (2006) Antimicrobial properties of salt (NaCl) used for the preservation of natural casings. *Food Microbiology* 23, 657-62.

Yoon S S, Hennigan R F, Hilliard G M, Ochsner U A, Parvatiyar K, Kamani M C, Allen H L, DeKievit R E, Gardner P R, Schwab T, Rowe J J, Iglewski B H, McDermott T R, Mason R P, Wozniak D J, Hancock R E W, Parsek M R, Noah T L, Boucher R C, Hassett D J (2002) *Pseudomonas aeruginosa* Anaerobic Respiration in Biofilms: Relationships to Cystic Fibrosis Pathogenesis. *Developmental Cell* 3, 593-603.

The invention claimed is:

1. Method of dental, endodontic or periodontal treatment or implant surgery in a subject, said method comprising the application of a disinfectant or antimicrobial preparation containing one or more tonicity agents in an amount which render the composition hypertonic, said preparation comprising a first tonicity agent selected from the group of organic acids and salts thereof.

2. Method according to claim 1, wherein the preparation comprises the sodium, potassium or magnesium salt of an organic acid.

3. Method according to claim 1, wherein the first tonicity agent is selected from the group consisting of sodium acetate, sodium sorbate, sodium lactate, sodium formate, potassium acetate, potassium sorbate, potasssium lactate and potassium formate.

4. Method according to claim 1, wherein the preparation comprises a further tonicity agent selected from the group consisting of inorganic salts and sugar alcohols.

5. Method according to claim 1, which is a method for treating and/or preventing apical, lateral and/or marginal periodontitis, gingivitis, peri-implantitis and/or other forms of oral infection.

6. Method according to claim 1, wherein said disinfectant or antimicrobial preparation is buffered to a pH of below 7.

7. Method according to claim 1, wherein the method comprises root canal treatment.

* * * * *